United States Patent

Krause et al.

Patent Number: 5,434,202
Date of Patent: Jul. 18, 1995

[54] N-(β-CARBONY- AND β-CYANOVINYL)-2,2,6,6-TETRAMETHYL-PIPERIDINE DERIVATIVES

[75] Inventors: Alfred Krause, Schwetzingen; Alexander Aumueller, Neustadt; Hubert Trauth, Dudenhofen, all of Germany

[73] Assignee: BASF Aktiengesellschaft, Ludwigshafen, Germany

[21] Appl. No.: 244,209

[22] PCT Filed: Nov. 27, 1992

[86] PCT No.: PCT/EP92/02733

§ 371 Date: Jun. 3, 1994

§ 102(e) Date: Jun. 3, 1994

[87] PCT Pub. No.: WO93/11109

PCT Pub. Date: Jun. 10, 1993

[30] Foreign Application Priority Data

Dec. 6, 1991 [DE] Germany ............ 41 40 304.5

[51] Int. Cl.⁶ .............. C08K 5/3435; C07D 211/46; C07D 211/58
[52] U.S. Cl. ..................... 524/103; 524/99; 524/102; 546/188; 546/216; 546/223; 546/224; 546/242; 546/246; 546/247
[58] Field of Search ............ 524/102, 103, 99; 546/188, 216, 223, 224, 242, 246, 247

[56] References Cited

U.S. PATENT DOCUMENTS

| | | | |
|---|---|---|---|
| 4,360,675 | 11/1982 | Nikles | 546/216 |
| 4,898,946 | 2/1990 | Costanzi | 546/216 |
| 5,290,940 | 3/1994 | Cunkle | 546/229 |

FOREIGN PATENT DOCUMENTS 18210 8/1994 WIPO .

OTHER PUBLICATIONS

Synthesis of 4-Piperidone Derivatives and Study of Their Pharmacological Properties, 1988 Plenum Publishing Corporation pp. 411–417 (1988).

*Primary Examiner*—Ceila Chang
*Attorney, Agent, or Firm*—Oblon, Spivak, McClelland, Maier & Neustadt

[57] ABSTRACT

N-(β-carbonyl- and β-cyanovinyl)-2,2,6,6-tetramethyl-piperidine derivatives of the formula I

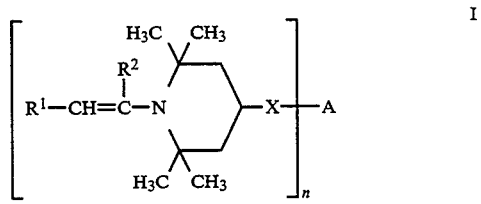

where
$R^1$ is $COOR^3$, $COR^4$, $CONR^4R^5$ or $CN$,
$R^2$ has the meanings of $R^1$ or is $C_1$–$C_{12}$-alkyl or hydrogen,
$R^3$ is hydrogen, $C_1$–$C_8$-alkyl, $C_5$–$C_8$-cycloalkyl, $C_3$–$C_5$-alkenyl or phenyl which can be mono- to trisubstituted by $C_1$–$C_4$-alkyl, $C_1$–$C_4$-alkoxy, $C_1$–$C_4$-alkoxycarbonyl, halogen, hydroxyl, phenoxy, phenyl, tolyl or xylyl,
$R^4$ and $R^5$ are each hydrogen, $C_1$–$C_{12}$-alkyl, $C_5$–$C_8$-cycloalkyl or phenyl which can be mono- to trisubstituted by $C_1$–$C_4$-alkyl, $C_1$–$C_4$-alkoxy, $C_1$–$C_4$-alkoxycarbonyl, halogen, hydroxyl, phenoxy, phenyl, tolyl or xylyl,
n is 1–4,
X and A for each individual n have been defined in the specification.

10 Claims, No Drawings

N-(β-CARBONY- AND β-CYANOVINYL)-2,2,6,6-TETRAMETHYL-PIPERIDINE DERIVATIVES

This application is a 35 U.S.C. § 371 filing of PCT/EP92/02733 filed Nov. 27, 1992.

The present invention relates to novel N-(β-carbonyl- and β-cyanovinyl)-2,2,6,6-tetramethylpiperidine derivatives of the formula I

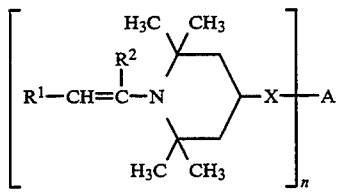

where
$R^1$ is $COOR^3$, $COR^4$, $CONR^4R^5$ or $CN$,
$R^2$ has the meanings of $R^1$ or is $C_1$-$C_{12}$-alkyl or hydrogen,
$R^3$ is hydrogen, $C_1$-$C_8$-alkyl, $C_5$-$C_8$-cycloalkyl, $C_3$-$C_5$-alkenyl or phenyl which can be mono- to trisubstituted by $C_1$-$C_4$-alkyl, $C_1$-$C_4$-alkoxy, $C_1$-$C_4$-alkoxycarbonyl, halogen, hydroxyl, phenoxy, phenyl, tolyl or xylyl,
$R^4$ and $R^5$ are each hydrogen, $C_1$-$C_{12}$-alkyl, $C_5$-$C_8$-cycloalkyl or phenyl which can be mono- to trisubstituted by $C_1$-$C_4$-alkyl, $C_1$-$C_4$-alkoxy, $C_1$-$C_4$-alkoxycarbonyl, halogen, hydroxyl, phenoxy, phenyl, tolyl or xylyl,
n is 1-4,
for the case n=1
X is oxygen, sulfur or —$NR^6$—, —$NR^6$—CO—,

—O—CO—, —O—CO—O—, —O—CO—$NR^6$— or —$NR^6$—CO—$NR^6$, where the linkage to position 4 of the piperidine ring takes place via an N or O in the stated group and
$R^6$ is hydrogen, $C_1$-$C_{20}$-alkyl, $C_5$-$C_8$-cycloalkyl, $C_7$-$C_{20}$-phenylalkyl or phenyl which can be mono- to trisubstituted by $C_1$-$C_4$-alkyl, halogen, phenyl or hydroxyl,
A is hydrogen, $C_1$-$C_{30}$-alkyl which can be interrupted by one or more non-adjacent oxygens, $C_2$-$C_{12}$-hydroxyalkyl, $C_1$-$C_{12}$-haloalkyl, $C_3$-$C_5$-epoxyalkyl, $C_2$-$C_{20}$-alkenyl, $C_2$-$C_6$-alkynyl, $C_5$-$C_8$-cycloalkyl, $C_7$-$C_{20}$-Phenylalkyl, phenyl which can be mono- to trisubstituted by $C_1$-$C_4$-alkyl, $C_1$-$C_4$-alkoxycarbonyl, halogen or hydroxyl or is —CH=CH—$COOR^3$ or $C_4$-$C_{30}$-alkyl which contains a heterocycle from the group comprising furan, tetrahydro furan, thiophene, imidazole, pyridine, piperidine, morpholine and α-piperidone as bridge or end group, or
X—A is

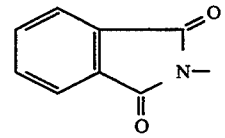

or

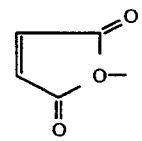

the case n=2
X has the same meanings as for the case n=1,
A is $C_1$-$C_{20}$-alkylene which can be interrupted by one or more non-adjacent oxygens or —$NR^7$— groups, or is $C_5$-$C_8$-cycloalkylene, $C_7$-$C_{20}$-phenylalkylene, o-, m- or p-phenylene which can be mono- to trisubstituted by $C_1$-$C_4$-alkyl, $C_1$-$C_4$-alkoxycarbonyl, halogen or hydroxyl, or is $C_4$-$C_{30}$-alkylene which contains a heterocycle from the group comprising furan, tetrahydrofuran, thiophene, imidazole, pyridine, piperidine, morpholine and α-piperidone as bridge, where
$R^7$ is $C_1$-$C_5$-alkyl or $C_5$-$C_8$-cycloalkyl, or
$X_2A$ is

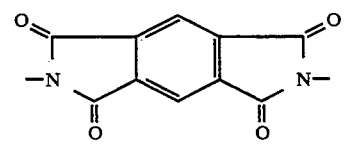

or

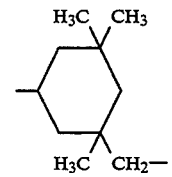

the case n=3
$X_3A$ is

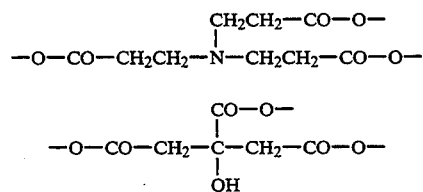

and
for the case n=4
$X_4A$ is

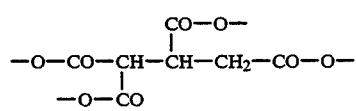

or

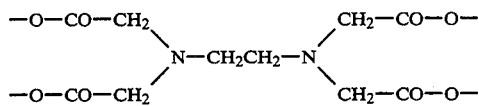

The present invention also relates to organic material stabilized against the action of light, oxygen and heat using the compounds I, especially stabilized synthetic materials and surface coatings.

Organic material, especially synthetic materials and surface coatings, is known to be very rapidly decomposed, especially by the action of light. This decomposition normally becomes manifest by yellowing, discoloration, fissuring or embrittlement of the material. The aim of stabilizers is therefore to protect organic material satisfactorily against decomposition by light, oxygen and heat.

Thus, EP-A 389419 (1) recommends polyalkylpiperidine derivatives which have a hydrocarbyloxy group on the piperidine nitrogen, and thus have a lower basicity than, for example, N-alkyl-substituted polyalkylpiperidine derivatives, as light stabilizers in high molecular weight compounds.

Prior art agents of this type are still often unsatisfactory owing to the low compatibility with synthetic materials, the short duration of the protective action, the intrinsic color of the substances, the tendency to volatility and the thermal decomposition of the stabilizers on incorporation at elevated temperature.

It is an object of the present invention to provide stabilizers which provide more effective protection for organic material.

We have found that this object is achieved by the $N$-($\beta$-carbonyl- and $\beta$-cyanovinyl)-2,2,6,6-tetramethylpiperidine derivatives I defined at the outset.

$R^1$ is preferably $COOR^3$.

$R^2$ is preferably $COOR^3$ or hydrogen.

$R^3$ is preferably $C_1$-$C_4$-alkyl, especially methyl or ethyl.

The value of n is preferably 1 or 2.

When $n=1$ and $n=2$, X is preferably oxygen or $-NR^6-$, $-NR^6-CO-$,

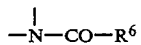

or $-O-CO-$, where $R^6$ is, in particular, hydrogen, $C_1$-$C_{12}$-alkyl, especially $C_1$-$C_4$-alkyl, cyclopentyl, cyclohexyl, benzyl, phenyl or tolyl.

For the case $n=1$, A is preferably hydrogen, $C_1$-$C_{18}$-alkyl, especially $C_1$-$C_{12}$-alkyl, $C_1$-$C_5$-methoxyalkyl, especially $\omega$-$C_3$-$C_5$-methoxyalkyl, $C_2$-$C_4$-hydroxyalkyl especially $\omega$-$C_2$-$C_4$-hydroxyalkyl, $C_1$-$C_4$-haloalkyl, especially halomethyl and haloethyl, $C_2$-$C_{18}$-alkenyl, especially $C_2$-$C_6$-alkenyl and $C_{15}$-$C_{18}$-alkenyl, cyclopentyl, cyclohexyl, benzyl, phenyl or tolyl.

For the case $n=2$, A is preferably $C_1$-$C_{12}$-alkylene, especially polymethylene of the formula $-(CH_2)_p-$ with $p=1-12$, $-(CH_2CH_2O)_m-CH_2CH_2-$ or $-(CH_2CH_2NR^7)_m-CH_2CH_2-$, where m is 1-9, preferably 1-5, and $R^7$ is $C_1$-$C_3$-alkyl or cyclohexyl, or is cyclopentylene, cyclohexylene, 1,3- or 1,4-bismethylenecyclohexane.

Suitable $C_1$-$C_3$-, $C_1$-$C_4$-, $C_1$-$C_5$-, $C_1$-$C_8$-, $C_1$-$C_{12}$-, $C_1$-$C_{18}$-, $C_1$-$C_{20}$- and $C_1$-$C_{30}$-alkyl radicals are branched and, in particular, straight-chain representatives, especially methyl, ethyl, n-propyl, isopropyl, n-butyl, isobutyl, sec.-butyl, tert.-butyl, n-amyl, isoamyl, sec.-amyl, tert.-amyl, neopentyl, n-hexyl, n-heptyl, n-octyl, 2-ethylhexyl, n-nonyl, isononyl, n-decyl, n-undecyl, n-dodecyl, n-tridecyl, isotridecyl, n-tetradecyl, n-pentadecyl, n-hexadecyl, n-heptadecyl, n-octadecyl, n-nonadecyl, n-eicosyl, n-pentacosyl and n-triacontyl.

Particularly suitable $C_5$-$C_8$-cycloalkyl radicals are cyclopentyl, cyclohexyl, cycloheptyl, cyclooctyl, methylcyclopentyl, dimethylcyclopentyl, methylcyclohexyl, dimethylcyclohexyl and ethylcyclohexyl.

Particularly suitable $C_3$-$C_5$-, $C_2$-$C_6$-, $C_{15}$-$C_{18}$-, $C_2$-$C_{18}$- and $C_2$-$C_{20}$-alkenyl radicals, which contain one or more, in particular one or two, olefinic double bonds, are vinyl, allyl, methallyl, crotyl, pentenyl, 1,3- and 2,4-pentadienyl, hexenyl or 8-heptadecenyl.

Examples of suitable $C_2$-$C_6$-alkynyl radicals are ethynyl and propynyl.

Suitable $C_1$-$C_4$-alkoxy radicals are, in particular, methoxy and ethoxy, but also n-propoxy, isopropoxy, n-butoxy, isobutoxy, sec.-butoxy and tert.-butoxy.

Examples of $C_1$-$C_4$-alkoxycarbonyl groups used are n-propoxycarbonyl, isopropoxycarbonyl, n-butoxycarbonyl, isobutoxycarbonyl, sec.-butoxycarbonyl, tert.-butoxycarbonyl, but especially ethoxycarbonyl and methoxycarbonyl.

The term halogen comprises fluorine, iodine but especially bromine and, in particular, chlorine.

Examples of suitable $C_7$-$C_{20}$-phenylalkyl groups are 1-phenylethyl, 2-phenylethyl, 1-phenylpropyl, 2-phenylpropyl, 3-phenylpropyl, 2-phenyl-2-propyl, 4-phenylbutyl, 2,2-dimethyl-2-phenylethyl, 5-phenylamyl, 10-phenyldecyl, 12-pohenyldodecyl, 14-phenyltetradecyl or, in particular, benzyl.

When monosubstituted phenyl radicals are used, the substitution pattern is ortho, meta or, preferably, para, the substituents in disubstituted phenyl radicals are especially in positions 2 and 4, e.g. 2,4-xylyl, and the substituents in trisubstituted phenyl radicals are in positions 2, 4 and 6, e.g. mesityl. When the substituents are present, the degree of substitution is preferably 1 or 2, especially 1.

Examples of $C_1$-$C_{30}$-alkyl interrupted by one or more non-adjacent oxygens are $C_1$-$C_5$-methoxyalkyl such as methoxymethyl, 2-methoxyethyl, 3-methoxypropyl, 4-methoxybutyl or 5-methoxypentyl, furthermore ethoxymethyl, 2-ethoxyethyl, 3-ethoxypropyl, 4-oxaheptyl, 3,6-dioxaheptyl, 3,6,9-trioxadecyl, 3,6,9,12-tetraoxatridecyl, 3,6,9,12,15-pentaoxahexadecyl, 3,6,9,12,15,18-hexaoxaeicosyl, $\omega$-ethoxymyristyl, $\omega$-butoxymyristyl, $\omega$-methoxycetyl, $\omega$-ethoxycetyl, $\omega$-butoxycetyl, $\omega$-methoxystearyl, $\omega$-ethoxystearyl or $\omega$-butoxystearyl.

Particularly suitable $C_2$-$C_{12}$- and $C_1$-$C_4$-hydroxyalkyl groups are 2-hydroxyethyl, 2-hydroxypropyl, 3-hydroxypropyl, 2-hydroxybutyl, 3-hydroxybutyl, 4-hydroxybutyl, 5-hydroxypentyl, 6-hydroxyhexyl, 7-hydroxyheptyl, 8-hydroxyoctyl, 9-hydroxynonyl, 10-hydroxydecyl, 11-hydroxyundecyl and 12-hydroxydodecyl.

Particularly suitable $C_1$-$C_{12}$- and $C_1$-$C_4$-haloalkyl is chloroalkyl, for example 2-chloroethyl, 2-chloropropyl, 3-chloropropyl, 2-chlorobutyl, 3-chlorobutyl, 4-chlorobutyl but especially chloromethyl, and it is furthermore possible to employ 5-chloropentyl, 6-chlorohexyl, 7-chloroheptyl, 8-chlorooctyl, 9- chlorononyl, 10-chlorodecyl, 11-chloroundecyl and 12-chlorododecyl.

Suitable examples of $C_3$-$C_5$-epoxyalkyl are 2,3-epoxybutyl, 3,4-epoxybutyl, 2,3-epoxypentyl, 3,4-epoxypentyl, 4,5-epoxypentyl and, in particular, 2,3-epoxypropyl.

If, in the case n=1, A is $C_4$-$C_{30}$-alkyl which contains a heterocycle as end group, particularly suitable structures for these radicals are as follows:

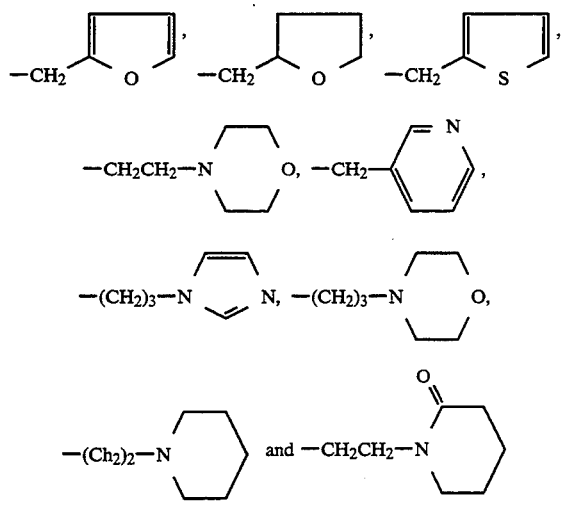

If, in the case n=1 and n=2, A is $C_4$-$C_{30}$-alkyl and $C_4$-$C_{30}$-alkylene, respectively, containing a heterocycle as bridge, the following structures are particularly suitable for these groups:

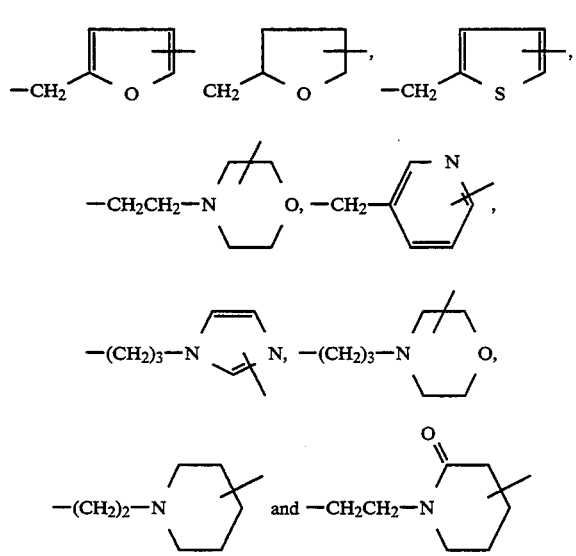

Particularly suitable as $C_1$-$C_{20}$- and $C_1$-$C_{12}$-alkylene are methylene, ethylidene, ethylene, propylidene, propylene, trimethylene, tetramethylene, pentamethylene, neopentylene, hexamethylene, heptamethylene, octamethylene, nonamethylene, decamethylene, 3,6-dimethyloctamethylene, undecamethylene, decamethylene, tetradecamethylene, hexadecamethylene, octadecamethylene and eicosamethylene.

Examples of $C_1$-$C_{20}$-alkylene interrupted by one or more non-adjacent oxygens or —$NR^7$-groups are 2-octatrimethylene, 2-oxatetramethylene, 2-oxapentamethylene, 3-oxapentamethylene, 4-oxaheptamethylene, 3,6-dioxaoctamethylene, 3,6,9-trioxaundecamethylene, 3,6,9,12-tetraoxatetradedecamethylene, 3,6,9,12,15-pentaoxaheptadecamethylene, 4-methylazaheptamethylene or 3,6-dimethylazaoctamethylene.

Particularly suitable $C_5$-$C_8$-cycloalkylene groups are cyclopentylene, cyclohexylene, cycloheptylene, cyclooctylene, methylcyclopentylene, dimethylcyclopentylene, methylcyclohexylene, dimethylcyclohexylene, ethylcyclohexylene, 1,3- or 1,4-bismethylenecyclohexane.

Suitable examples of $C_7$-$C_{20}$-phenylakylene are 1-phenylethylene, 1-phenylpropylene, 1-phenyltrimethylene, 2-phenylpropylene, 2-phenyltrimethylene, 2-phenyltetramethylene, 3-phenylpentamethylene, 3-phenylhexamethylene or, in particular phenylmethylene.

There is in principle no restriction on the configuration at the double bond of I with regards the position of $R^1$ with respect to the piperidine ring and to $R^2$. Both the E and the Z isomers and, in the case $R^2$=H, both the cis and the trans isomers are possible. It is, of course, also possible for mixtures of the cis/trans and E/Z isomers to be present.

The N-($\beta$-carbonyl- and $\beta$-cyanovinyl)-2,2,6,6-tetramethylpiperidine derivatives I according to the invention can be prepared in an advantageous way by reacting the corresponding piperidine derivatives which are not substituted on the piperidine nitrogen, of the formula II

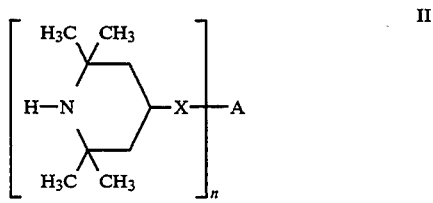

with an acetylenic compound of the formula III

III

Examples of suitable acetylenic compounds III are esters of dicarboxylic acids, such as dimethyl and diethyl acetylene dicarboxylate, esters of monocarboxylic acids, such as methyl and ethyl propiolate, or cyanoacetylene.

The compounds III are Michael acceptors which particularly easily undergo addition onto nucleophiles such as piperidines.

The N-($\beta$-carbonyl- and $\beta$-cyanovinyl)-2,2,6,6-tetramethylpiperidine derivatives I according to the invention can also in principle be prepared in an advantageous way by reacting the corresponding piperidine derivatives which are not substituted on the piperidine nitrogen and not yet functionalized in position 4, of the formula IV

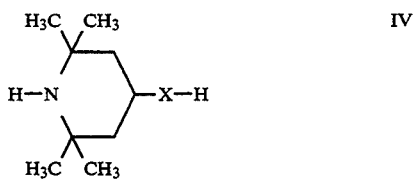

e.g. 4-hydroxy-2,2,6,6-tetramethylpiperidine, with an acetylenic compound III and subsequently functionalizing the X—H to $X_nA$.

The Michael addition of acetylenic monocarboxylic and dicarboxylic esters onto 2,2,6,6-tetramethyl-4-piperidone to give N-($\beta$-alkoxycarbonylvinyl) -2,2,6,6-tetramethyl-4-piperidones V

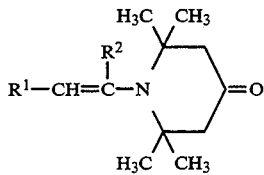

is disclosed in reference (2) Khim. Farm. Zh. 21 (1987), 411–413. However, (2) makes no reference to the possible suitability of the compounds V as stabilizers.

Thus, in the case X=O, it is also possible to prepare the N-($\beta$-carbonyl- and $\beta$-cyanovinyl)-2,2,6,6-tetramethylpiperidine derivatives I according to the invention by catalytic hydrogenation or reduction, e.g. using sodium borohydride, of the compounds V to give the corresponding 4-hydroxypiperidine derivatives and subsequent functionalization of the O—H to $O_nA$.

It is also possible in principle to prepare N-($\beta$-carbonyl- and $\beta$-cyanovinyl)-2,2,6,6-tetramethylpiperidine derivatives I according to the invention, where X is an N-containing group, from the ketones V by reductive amination.

Suitable for the functionalization of the compounds with X—H, in particular with O—H, to compounds with $X_nA$, in particular $O_nA$, are the carboxylic acids, carboxylic acid derivatives, carbonic acid derivatives, mono- or diisocyanates or alkylating, alkenylating or aralkylating agents containing the groups required in A.

The carboxylic acids or carboxylic acid derivatives which can be employed for this are, in particular, mono- or dibasic carboxylic acids such as formic acid, acetic acid, succinic acid or adipic acid, halides of such acids, such as acetyl chloride, chloroacetyl chloride, acryloyl chloride, methacryloyl chloride, isobutyryl chloride, oleoyl chloride, lauroyl chloride, stearoyl chloride, benzoyl chloride or benzoyl bromide, oxalyl chloride, malonyl dichloride, succinyl dichloride, adipyl dichloride or sebacyl dichloride, esters of such acids, such as methyl acetate, ethyl acetate, methyl propionate, methyl butyrate, diethyl malonate, diethyl fumarate, dimethyl adipate, dimethyl suberate or dimethyl sebacate, as well as mono- or dichloroformates such as methyl chloroformate, ethyl chloroformate, butanediol dichloroformate or hexanediol dichloroformate.

Examples of suitable carbonic acid derivatives for the said purpose are dimethyl carbonate, diethyl carbonate and phosgene.

particularly suitable mono- or diisocyanates for generating urethane groups in the compounds I are $C_2$-$C_{18}$-alkyl mono- and diisocyanates, e.g. stearyl isocyanate and hexamethylene diisocyanate, furthermore phenyl isocyanate, phenylene 1,4-diisocyanate, toluylene 2,4-diisocyanate and isophorone diisocyanate.

Used as alk(en)ylating or aralkylating agents are, in particular, the corresponding alk(en)yl and aralkyl halides, especially chlorides and bromides, tosylates and sulfates, e.g. dimethyl sulfate or diethyl sulfate.

All these variations are expediently carried out in an organic solvent which is inert towards the reaction system, e.g. a hydrocarbon such as n-hexane, cyclohexane, benzene, toluene, xylene or mesitylene, a chlorohydrocarbon such as methylene chloride, chloroform, tetrachloromethane or chlorobenzene, an alcohol such as methanol, ethanol, isopropanol or butyl glycol or an ester such as ethyl acetate, methyl benzoate or butyl glycol acetate. It is also possible to employ an alcohol/water mixture, e.g. methanol/water, ethanol/water or isopropanol/water, as solvent for the said reactions with good results.

The reactions are usually carried out at room temperature or above, expediently at from 0° to 200° C., preferably at from 10° to 140° C. Some of the reactions are carried out in the presence of an amine as base or catalyst, for example in the isocyanate reactions and the reactions between compounds with X—H and carboxylic acids or carboxylic acid derivatives; particularly suitable as such bases or catalysts are tertiary amines such as trimethylamine, triethylamine, triisopropylamine, tri-n-butylamine, diazabicyclooctane or pyridine.

The N-($\beta$-carbonyl- and $\beta$-cyanovinyl)-2,2,6,6-tetramethylpiperidine derivatives according to the invention are outstandingly suitable for the stabilization of organic materials against the action of light, oxygen and heat. They are added to the organic materials to be stabilized in a concentration of from 0.01 to 5%, preferably from 0.02 to 1%, of the weight of the organic material, before, during or after its production.

By organic materials are meant, for example, cosmetic preparations such as ointments, lotions, drug formulations such as pills and suppositories, photographic recording material such as photographic emulsions or precursors for synthetic materials and surface coatings, but especially synthetic materials and surface coatings themselves.

The present invention also relates to organic material, especially synthetic materials and surface coatings, containing the compounds I in the concentrations indicated above and stabilized against the action of light, oxygen and heat.

The compounds I according to the invention can be mixed, in particular, with synthetic materials using all conventional equipment and methods for mixing stabilizers or other additives into polymers.

The organic material stabilized by the compounds I according to the invention can also contain further additives, e.g. antioxidants, light stabilizers, metal inactivators, antistatic agents, flame retardants, pigments and fillers.

Examples of antioxidants and light stabilizers which can be added in addition to the compounds according to the invention are compounds based on sterically hindered phenols or sulfur- or phosphorus-containing costabilizers.

Examples of such phenolic antioxidants are 2,6-di-tert.-butyl-4-methylphenol, n-octadecyl $\beta$-(3,5-di-tert.-butyl-4-hydroxyphenyl) propionate, 1,1,3-tris(2-methyl-4-hydroxy-5-tert.-butylphenyl)butane, 1,3,5-trimethyl2,4,6-tris(3,5-di-tert.-butyl-4-hydroxybenzyl)benzene, tris(3,5-di-tert.-butyl-4-hydroxybenzyl) isocyanurate, tris[$\beta$-(3,5-di-tert.-butyl-4-hydroxyphenyl)propionylethyl] isocyanurate, tris(2,6-dimethyl-3-hydroxy-4-tert.-butylbenzyl)isocyanurate and pentaerythritol tetrakis[$\beta$-(3,5-di-tert.-butyl-4-hydroxyphenyl)propionate].

Examples of suitable phosphorus-containing antioxidants are tris( nonylphenyl) phosphite, distearylpentaerythritol diphosphite, tris (2,4-di-tert.-butylphenyl)- phosphite, tris(2-tert.-butyl-methylphenyl) phosphite, bis(2,4-di-tert.-butylphenyl)pentaerythritol diphosphite and tetrakis(2,4-di-tert.-butylphenyl)-4,4'-biphenylene diphosphite.

Examples of sulfur-containing antioxidants are dilauryl thiodipropionate, dimyristyl thiodipropionate, distearyl thiodipropionate, pentaerythritol tetrakis(β-laurylthiopropionate) and pentaerythritol tetrakis(β-hexylthiopropionate).

Examples of other antioxidants and light stabilizers which can be used together with compounds I according to the invention are 2-(2-hydroxyphenyl)benzotriazoles, 2-hydrobenzophenones, aryl esters of hydroxybenzoic acids, α-cyanocinnamic acid derivatives, benzimidazolecarboxanilides, nickel compounds and oxanilides.

Examples of synthetic materials which can be stabilized by the compounds I according to the invention are:

Polymers of mono- and diolefins such as low or high density polyethylene, polypropylene, linear poly-1-butene, polyisoprene, polybutadiene and copolymers of mono- or diolefins or mixtures of the said polymers;

Copolymers of mono- or diolefines with other vinyl monomers such as ethylene/alkyl acrylate copolymers, ethylene/alkyl methacrylate copolymers, ethylene vinyl acetate copolymers or ethylene/acrylic acid copolymers;

Polystyrene and copolymers of styrene or α-methylstyrene with dienes and/or acrylic derivatives such as styrene/butadiene, styrene/acrylonitrile (SAN), styrene/ethyl methacrylate, styrene/butadiene ethyl acrylate, styrene/acrylonitrile methacrylate, acrylonitrile/butadiene/styrene (ABS) or methyl methacrylate/butadiene/styrene (MBS);

Halogen-containing polymers such as polyvinyl chloride, polyvinyl fluoride, polyvinylidene fluoride and copolymers thereof;

Polymers derived from α,β-unsaturated acids and their derivatives, such as polyacrylates, polymethacrylares, polyacrylamides and polyacrylonitriles;

Polymers derived from unsaturated alcohols and amines or from their acyl derivatives or acetals, e.g. polyvinyl alcohol and polyvinyl acetate;

Polyurethanes, polyamides, polyureas, polyesters, polycarbonates, polysulfones, polyether-sulfones and polyether-ketones.

The compounds I according to the invention can furthermore be used to stabilize surface coatings, e.g. industrial paints. Of these, storing paints are particularly emphasized, and of these in turn automotive paints, preferably two-layer paints. Another area of use comprises, for example, external paints for buildings, other edifices or industrial equipment.

The compounds I according to the invention can be added in solid or dissolved form to the surface coating. Their good solubility in coating systems is particularly advantageous.

The compounds I according to the invention are preferably used to stabilize polyamides and ABS and SAN polymers, especially molding compositions composed of these, and surface coatings.

Another preferred area of use is the stabilization of polypropylene and polyamide, especially of fibers composed of these.

The compounds I according to the invention are very compatible with the conventional types of synthetic material and have high solubility and excellent compatibility with conventional coating systems. They have as a rule little or no intrinsic color, are stable and involatile at the temperatures customary for processing synthetic materials and surface coatings and, above all, protect the materials treated with them for a long time.

The invention is illustrated by the following examples. The preparation conditions have not been optimized.

PREPARATION EXAMPLES

Example 1a

Ethyl β-(2,2,6,6-tetramethyl-4-hydroxy-1-piperidinyl)acrylate from 2,2,6,6-tetramethyl-4-hydroxypiperidine 54 g (0.55 mol) of ethyl propiolate were added dropwise to 78 g (0.50 mol) of 2,2,6,6-tetramethyl-4-hydroxypiperidine in 250 ml of butylglycol acetate at 80° C. at a rate such that the temperature did not exceed 100° C. The mixture was then heated at 100° C. for a further 4 hours. After cooling to room temperature, the precipitated product was filtered off, thoroughly washed with petroleum ether and subsequently dried at 60° C. under 0.1 mbar. 104 g (corresponding to a yield of 82%) of the compound of the formula

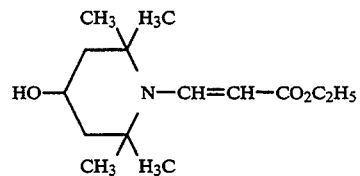

were obtained in the form of a colorless solid of melting point 106° C.

When the reaction was carried out at from 50° to 60° C. in 150 ml of an ethanol/water mixture in the ratio 1:1 by volume and the product was precipitated by stirring the reaction mixture into 300 ml of water, filtered off, washed with water and dried at 60° C. and under 0.1 mbar, the title compound was obtained in a yield of 92% with the same purity.

Example 1b

Ethyl β-(2,2,6,6-tetramethyl-4-hydroxy-1-piperidinyl)acrylate by reduction of ethyl β-(2,2,6,6-tetramethyl-4-oxo-1-piperidinyl)acrylate The same piperidine derivative as in Example 1a was synthesized via the corresponding ketone.

54 g (0.55 mol) of ethyl propiolate were added dropwise to 78 g (0.50 mol) of triacetoneamine in 200 ml of ethanol at reflux, and the mixture was then stirred at this temperature for a further 4 hours. After cooling, the precipitated product was filtered off, thoroughly washed with petroleum ether and subsequently dried at 60° C. and under 0.1 mbar. 80 g (corresponding to a yield of 63%) of ethyl β-(2,2,6,6-tetramethyl-4-oxo-1-piperidinyl)acrylate were obtained in the form of a colorless solid of melting point 145° C.

15 g of sodium borohydride were added a little at a time to 80 g (0.32 mol) of the resulting ketone in 300 ml of ethanol at room temperature. After the mixture had been stirred at room temperature for 3 hours it was diluted with water, and the precipitate was filtered off and dried. 69.4 g (corresponding to a yield of 85%) of the title compound were obtained as a colorless solid of melting point 105°–106° C.

Example 2a

Dimethyl 2-(2,2,6,6-tetramethyl-4-hydroxy-1-piperidinyl)butene-1,2-dioate 35.5 g (0.25 mol) of dimethyl acetylenedicarboxylate and 38.7 g of 2,2,6,6-tetramethyl-4-hydroxypiperidine were heated in 300 ml of toluene at 70° C. for 3 hours. The solvent was removed by distillation under reduced pressure, and the resulting oil was crystallized from n-heptane. The product was filtered off, washed with petroleum ether and dried. 63 g (corresponding to a yield of 84%) of the compound of the formula

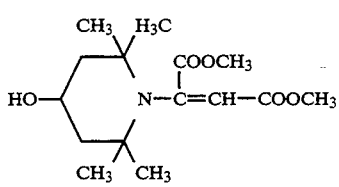

were obtained in the form of a colorless solid of melting point 58° C.

Example 2b

Dimethyl 2-(2,2,6,6-tetramethyl-4-hydroxy-1-piperidinyl)butene-1,2-dioate by reduction of dimethyl 2-(2,2,6,6-tetramethyl-4-oxo-1-piperidinyl)butene-1,2-dioate The same piperidine derivative as in Example 2a was synthesized via the corresponding ketone.

28.4 g (0.2 mol) of dimethyl acetylenedicarboxylate and 31.2 g of triacetoneamine in 200 ml of methanol were refluxed for 4 hours. The solvent was removed by distillation, and the resulting oil was crystallized from n-heptane. The product was filtered off, washed with petroleum ether and dried. 45 g (corresponding to a yield of 75%) of dimethyl 2-(2,2,6,6-tetramethyl-4-oxo-1-piperidinyl)butene-1,2-dioate were obtained in the form of a colorless solid of melting point 63°-64° C.

The reduction to the title compound with sodium borohydride was carried out as in Example 1a. The title compound was obtained in a yield of 78%.

Example 3

Ethyl β-(2,2,6,6-tetramethyl-4-acetoxy-1-piperidinyl)acrylate 11.8 g (0.15 mol) of acetyl chloride in 40 ml of methylene chloride were added dropwise to a mixture of 25.5 g (0.1 mol) of the compound from Example 1, 8.8 g (0.11 mol) of pyridine and 100 ml of methylene chloride at room temperature. The mixture was then refluxed for 2 hours. After cooling to room temperature, it was diluted with 200 ml of water, the organic phase was extracted with about 1% by weight hydrochloric acid and several times with water, dried over sodium sulfate and then stirred under reduced pressure to remove the solvent. 27 g of the compound with the formula shown below were obtained in the form of a pale yellow solid (corresponding to a yield of 90%) with a melting point of 55°-57° C.

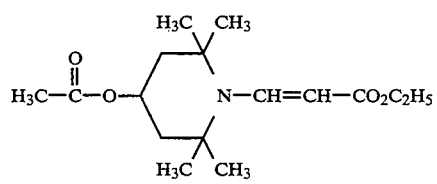

Example 4

Ethyl β-(2,2,6,6-tetramethyl-4-chloroacetoxy-1-piperidinyl)acrylate 17.0 g (0.15 mol) of chloroacetyl chloride in 40 ml of methylene chloride were added dropwise to a mixture of 25.5 g (0.1 mol) of the compound from Example 1, 8.8 g (0.11 mol) of pyridine and 100 ml of methylene chloride at room temperature. The mixture was then refluxed for 2 hours. After cooling to room temperature, it was diluted with 200 ml of water, and the organic phase was extracted with about 1% by weight hydrochloric acid and several times with water, dried over sodium sulfate and then distilled under reduced pressure to remove the solvent. 30 g of the compound with the formula shown below were obtained in the form of a yellow solid of melting point 80°-82° C.

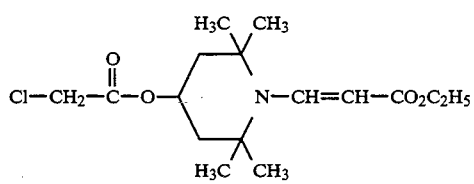

Example 5

Bis[2,2,6,6-tetramethyl-1-(trans-β-ethoxycarbonylvinyl)-4-piperidinyl] adipate 9.15 g of adipoyl dichloride were added dropwise to a solution of 28.05 g of the alcohol from Example 1 and 8.7 g of pyridine in 100 ml of methylene chloride at room temperature. The mixture was stirred at room temperature for 3 hours and then the precipitate was filtered off, and the organic phase was washed with about 1% by weight hydrochloric acid and with water, dried over magnesium sulfate and distilled under reduced pressure to remove the solvent. 26.8 g of the compound with the formula shown below were obtained in the form of a yellow solid. After recrystallization from butylglycol, the compound melted at 114°-116° C.

Analysis: Calculated: 65.8% C, 9.0% H, 4.5% N, 20.6% O; Found: 65.0% C, 9.2% H, 4.5% N, 20.7% O.

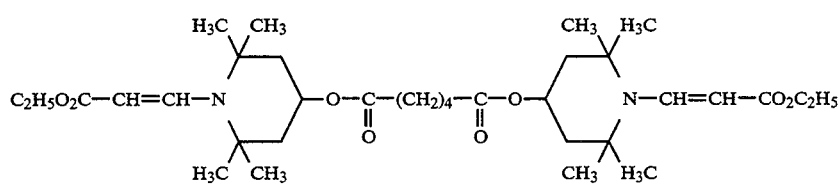

Example 6

Bis[2,2,6,6-tetramethyl-1-(trans-β-ethoxycarbonyl-vinyl)-4-piperidinyl] sebacate The synthesis was carried out as in Example 5 but with sebacoyl dichloride and resulted in the compound with the formula shown below in the form of a colorless solid of melting point 106°–108° C.

Analysis: Calculated: 67.5% C, 9.5% H, 4.1% N, 18.9% O; Found: 67.4% C, 9.6% H, 4.1% N, 18.7% O.

Analysis: Calculated: 66.8% C, 9.7% H, 14.8% O, 8.7% N; Found: 66.8% C, 9.8% H, 15.1% O, 8.6% N.

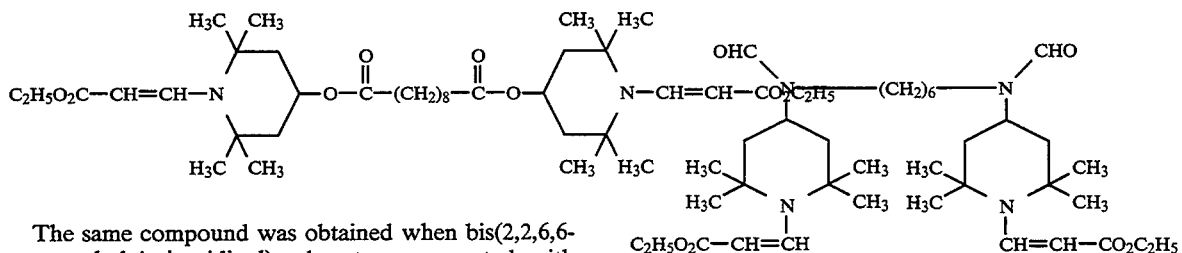

The same compound was obtained when bis(2,2,6,6-tetramethyl-4-piperidinyl) sebacate was reacted with two equivalents of ethyl propiolate in butylglycol acetate at 80°–100° C.

Example 7

Ethyl β-[2,2,6,6-tetramethyl-4-(N-formyl-N-octylamino)-1-piperidinyl]acrylate 59.2 g of 4-(N-formyl-N-octylamino)-2,2,6,6-tetramethylpiperidine and 20 g of ethyl propiolate were refluxed in 500 ml of toluene for 20 hours. Removal of the solvent by distillation under reduced pressure resulted in 80 g of the compound of the formula shown below in the form of a dark oil which crystallized after a few days to give a solid at melting point 58°–60° C.

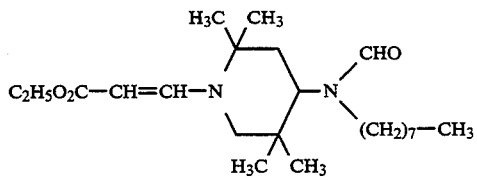

Example 8

N,N'-diformyl-N,N'-bis[1-(β-ethoxycarbonylvinyl)-2,2,6,6-tetramethyl-4-piperidinyl]hexamethylenediamine 43.5 g of ethyl propiolate were added dropwise to 100 g of hexamethylenebis(N-formyltriacetonediamine) in 400 ml of ethanol at the boiling point. Removal of the solvent by distillation under reduced pressure resulted in 95.3 g of the compound of the formula shown below in the form of a colorless solid of melting point 172° C.

Example 9

N-cyclohexyl-N-[1-(β-ethoxycarbonylvinyl)-2,2,6,6-tetramethyl-1-piperidinyl]oleamide A solution of 150.4 g of oleoyl chloride in 100 ml methylene chloride was added dropwise to a solution of 119 g of 4-cyclohexylamino-2,2,6,6-tetramethylpiperidine and 55.5 g of triethylamine in 250 ml of methylene chloride at room temperature. The mixture was then stirred at this temperature for 7 hours. The organic phase was washed several times with water and dried over sodium sulfate, and the solvent was removed by distillation under reduced pressure. The resulting oil was taken up in 600 ml of butylglycol acetate and heated to 100° C. 50 g of ethyl propiolate were added dropwise at this temperature, and the mixture was then stirred at this temperature for a further 6 hours. The oil resulting from removal of the solvent by distillation under reduced pressure was purified by chromatography on silica gel with ethyl acetate/n-hexane (1:3) to yield the compound of the formula

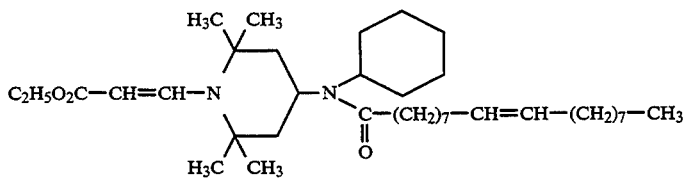

Example 10

Bis[1-(β-ethoxycarbonylvinyl)-2,2,6,6-tetramethyl-4-piperidinyl] malonate 150 g of ethyl propiolate were added dropwise to a solution of 270 g of bis(2,2,6,6-tetramethyl-4-piperidinyl) malonate in 400 ml of ethanol at 60° C. The mixture was then refluxed for 4 hours. The solvent was removed by distillation under reduced pressure, and recrystallization of the resulting residue from isopropanol yielded 245 g of the compound of the formula shown below in the form of a colorless solid of melting point 100°–102° C.

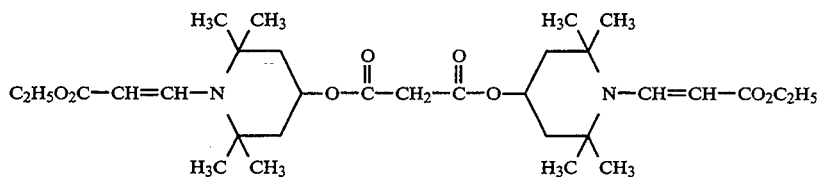

Example 11

Bis[1-β-ethoxycarbonylvinyl-2,2,6,6-tetramethyl-4-piperidinyl] fumarate 44 g of ethanol propiolate were added dropwise to a solution of 78.4 g of bis(2,2,6,6-tetramethyl-4-piperidinyl) fumarate in 300 ml of ethanol at 40° to 60° C. The mixture was then refluxed for 3 hours. The precipitate which resulted on cooling to room temperature was filtered off, washed with petroleum ether and dried. 107 g of the compound of the formula shown below were obtained in the form of a colorless solid of melting point 185°–186° C.

Example 13

N-[1-(β-ethoxycarbonylvinyl)-2,2,6,6-tetramethyl-4-piperidinyl]acrylamide

The title compound with the formula shown below was prepared in a similar manner to Example 12 from N-(2,2,6,6-tetramethyl-4-piperidinyl)acrylamide and ethyl propiolate in a yield of 81% in the form of a colorless solid of melting point 123°–125° C.

Analysis: Calculated: 66.2% C, 9.15% H, 15.6% O, 9.1% N; Found: 65.7% C, 9.2% H, 15.9% O, 9.0% N.

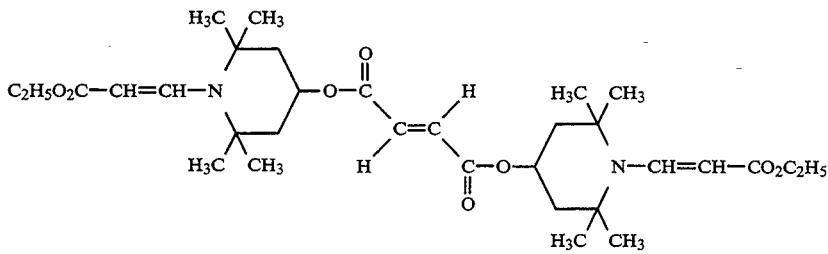

Example 12

1-(β-methoxycarbonylvinyl)-2,2,6,6-tetramethyl-4-piperidinyl acrylate 70 g of ethyl propiolate were added dropwise to a solution of 132 g of 2,2,6,6-tetramethyl-4-piperidinyl acrylate in 500 ml of ethanol at 50° C. The mixture was then refluxed for 3 hours. The solvent was removed by distillation under reduced pressure, and the resulting residues was recrystallized from an ethanol/water mixture in the ratio 2:3 by volume to yield 160 g of the compound of the formula shown below in the form of a colorless solid of melting point 54°–55° C.

Analysis: Calculated: 66.0% C, 8.8% H, 20.7% O, 4.5% N; Found: 66.1% C, 8.8% H, 20.5% O, 4.5% N.

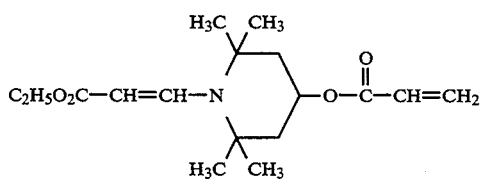

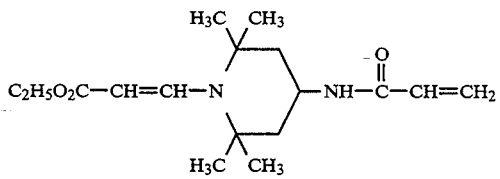

Example 14

1-(β-ethoxycarbonylvinyl)-2,2,6,6-tetramethyl-4-piperidinyl) sorbate 11 g of ethyl propiolate were added dropwise to a solution of 25.1 g of 2,2,6,6-tetramethyl-4-piperidinyl sorbate in 200 ml of ethanol at room temperature. After the vigorous evolution of heat which occurred during this had subsided the mixture was refluxed for 2 hours. The solvent was removed by distillation under reduced pressure, and recrystallization of the resulting residue from isobutanol yield 17.5 g of the compound of the formula shown below in the form of a colorless solid of melting point 90° C.

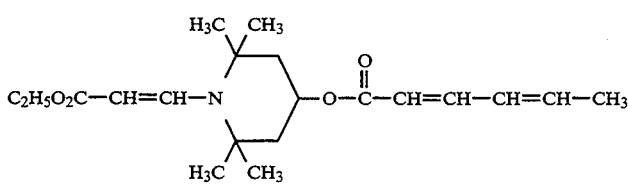

Example 15

1-(β-ethoxycarbonylvinyl)-2,2,6,6-tetramethyl-1-piperidinyl N-octadecylcarbamate 19.7 g of octadecyl isocyanate dissolved in 25 ml of toluene were added dropwise to a solution of 15.3 g of the compound from Example 1 and 0.5 g of 1,4-diazabicyclo[2.2.2]octane in 50 ml of toluene at 80° C. The mixture was then refluxed for 8 hours, cooled to room temperature and then washed twice with water, dried over sodium sulfate and distilled under reduced pressure to remove the solvent. Recrystallization of the resulting residue from methanol yielded 26 g of the compound of the formula shown below in the form of a colorless solid of melting point 70°–72° C.

Analysis: Calculated: 71.95% C, 11.3% H, 11.6% O, 5.1% N; Found: 72.0% C, 11.5% H, 11.5% O, 5.2% N.

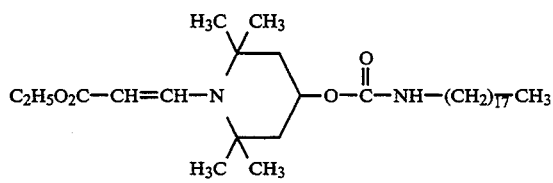

Example 16

Bis[1-(β-ethoxycarbonylvinyl)-2,2,6,6-tetramethyl-4-piperidinyl] hexamethylenebiscarbamate 16.8 g of hexamethylene diisocyanate dissolved in 50 ml of toluene were added dropwise to a solution of 53.55 g of the compound from Example 1 and 0.5 g of 1,4-diazabicyclo[2.2.2]octane in 150 ml of toluene at 80° C. The mixture was then refluxed for 14 hours and cooled to room temperature, and the resulting precipitate was filtered, washed with petroleum ether and dried. 54 g of the compound with the formula shown below were obtained the form of a colorless solid of melting point 186°–188° C.

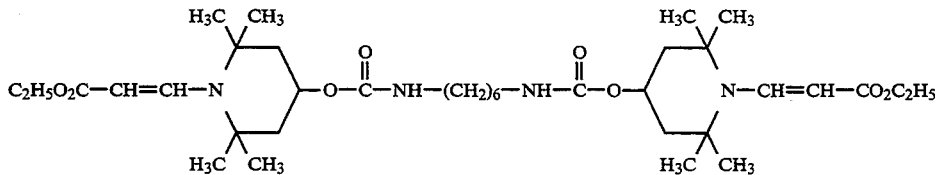

We claim:

1. An N-(β-carbonyl- and β-cyanovinyl)-2,2,6,6-tetramethylpiperidine derivative of the formula I

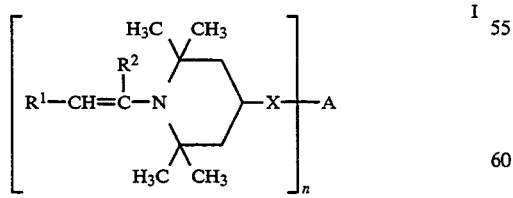

where
$R^1$ is $COOR^3$, $COR^4$, $CONR^4R^5$ or CN,
$R^2$ has the meanings of $R^1$ or is $C_1$–$C_{12}$-alkyl or hydrogen,
$R^3$ is hydrogen, $C_1$–$C_8$-alkyl, $C_5$–$C_8$-cycloalkyl, $C_3$–$C_5$-alkenyl or phenyl which can be mono- to trisubstituted by $C_1$–$C_4$-alkyl, $C_1$–$C_4$-alkoxy, $C_1$–$C_4$-alkoxycarbonyl, halogen, hydroxyl, phenoxy, phenyl, tolyl or xylyl, $R^4$ and $R^5$ are each hydrogen, $C_1$–$C_{12}$-alkyl, $C_5$–$C_8$-cycloalkyl or phenyl which can be mono- to trisubstituted by $C_1$–$C_4$-alkyl, $C_1$–$C_4$-alkoxy, $C_1$–$C_4$-alkoxycarbonyl, halogen, hydroxyl, phenoxy, phenyl, tolyl or xylyl, n is 1–4, for the case n=1

X is oxygen, sulfur or —$NR^6$—, —$NR^6$—CO—,

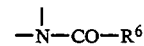

—O—CO—, —O—CO—O—, —O—CO—$NR^6$— or —$NR^6$—CO—$NR^6$, where the linkage to position 4 of the piperidine ring takes place via an N or O in the stated group and $R^6$ is hydrogen, $C_1$–$C_{20}$-alkyl, $C_5$–$C_8$-cycloalkyl, $C_7$–$C_{20}$-phenylalkyl or phenyl which can be mono- to trisubstituted by $C_1$–$C_4$-alkyl, halogen, phenyl or hydroxyl, A is hydrogen, $C_1$–$C_{30}$-alkyl which can be interrupted by one or more non-adjacent oxygens, $C_2$–$C_{12}$-hydroxyalkyl, $C_1$–$C_{12}$-haloalkyl, $C_3$–$C_5$-epoxyalkyl, $C_2$–$C_{20}$-alkenyl, $C_2$–$C_6$-alkynyl, $C_5$–$C_8$-cycloalkyl, $C_7$–$C_{20}$-phenylalkyl, phenyl which can be mono- to trisubstituted by $C_1$–$C_4$-alkyl, $C_1$–$C_4$-alkoxycarbonyl, halogen or hydroxyl or is —CH=CH—COOR$^3$ for the case n=2

X has the same meanings as for the case n=1,

A is $C_1$–$C_{20}$-alkylene which can be interrupted by one or more non-adjacent oxygens or —$NR^7$— groups, or is $C_5$–$C_8$-cycloalkylene, $C_7$–$C_{20}$-phenylalkylene, o-, m- or p-phenylene which can be mono- to trisubstituted by $C_1$–$C_4$-alkyl, $C_1$–$C_4$-alkoxycarbonyl, halogen or hydroxyl, where $R^7$ is $C_1$–$C_5$-alkyl or $C_5$–$C_8$-cycloalkyl, for the case n=3

$X_3A$ is

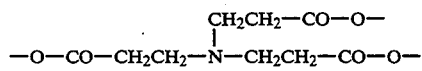

and

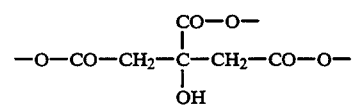

and for the case n=4

$X_4A$ is

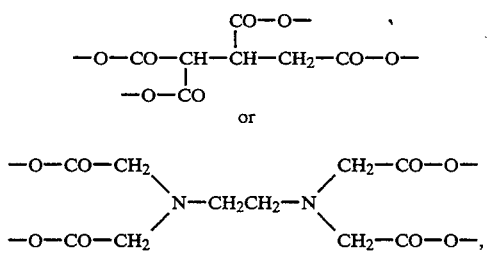

or

2. An N-(β-carbonyl- or β-cyanovinyl) -2,2,6,6-tetramethylpiperidine derivative I as claimed in claim 1, where $R^1$ is $COOR^3$.

3. An N-(β-carbonyl- or β-cyanovinyl)-2,2,6,6-tetramethylpiperidine derivative I as claimed in claims 1 or 2, where $R^2$ is $COOR^3$ or hydrogen.

4. An N-(β-carbonyl- or β-cyanovinyl) -2,2,6,6-tetramethylpiperidine derivative I as claimed in claim 2, where $R^3$ is $C_1$-$C_4$-alkyl.

5. An N-(β-carbonyl- or β-cyanovinyl)-2,2,6,6-tetramethylpiperidine derivative I as claimed in claims 1–4, where n is 1 or 2.

6. An N-(β-carbonyl- or β-cyanovinyl)-2,2,6,6-tetramethylpiperidine derivative I as claimed in claim 5, where X is oxygen or $-NR^6-$, $-NR^6-CO-$,

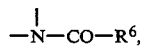

$-O-CO-$, where $R^6$ is hydrogen, $C_1$-$C_{12}$-alkyl, cyclopentyl, cyclohexyl, benzyl, phenyl or tolyl.

7. An N-(β-carbonyl- or β-cyanovinyl)-2,2,6,6-tetramethylpiperidine derivative I as claimed in claims 5 or 6, where in the case n=1 A is hydrogen, $C_1$-$C_{18}$-alkyl, $C_1$-$C_5$-methoxyalkyl, $C_2$-$C_4$-hydroxyalkyl, $C_1$-$C_4$-haloalkyl, $C_2$-$C_{18}$-alkenyl, cyclopentyl, cyclohexyl, benzyl, phenyl or tolyl.

8. An N-(β-carbonyl- or β-cyanovinyl)-2,2,6,6-tetramethylpiperidine derivative I as claimed in claims 5 or 6, where in the case n=2 A is $C_1$-$C_{12}$-alkylene, $-(CH_2CH_2O)_m-CH_2CH_2-$ or $-(CH_2CH_2NR^7-)_m-CH_2CH_2-$, where m is 1–9 and $R^7$ is $C_1$-$C_3$-alkyl or cyclohexyl, or is cyclopentylene, cyclohexylene, 1,3- or 1-4-bismethylenecyclohexane.

9. Organic material selected from the group consisting of:
   (a) polymers of mono- and diolefins,
   (b) copolymers of mono- or diolefins with vinyl monomers,
   (c) polystyrene and copolymers of styrene or α-methyl styrene with dienes and/or acrylic derivatives.
   (d) halogen-containing polymers
   (e) polymers derived from α,β-unsaturated acids,
   (f) polymers derived from unsaturated alcohols and amines or from their acyl derivatives or acetals,
   (g) polyurethanes, polyamides, polyureas, polyesters, polycarbonates, polysulfones, polyether-sulfones and polyether-ketones, stabilized against the action of light, oxygen and heat, containing 0.01–5% by weight, based on the amount of organic material, of one or more N-(β-carbonyl- or β-cyanovinyl) -2,2,6,6-tetramethylpiperidine derivatives I as claimed in claims 1–8.

10. A method for the stabilization of organic material selected from the group consisting of:
   (a) polymers of mono- and diolefins,
   (b) copolymers of mono- or diolefins with vinyl monomers,
   (c) polystyrene and copolymers of styrene or α-methyl styrene with dienes and/or acrylic derivatives,
   (d) halogen-containing polymers
   (e) polymers derived from α,β, unsaturated acids,
   (f) polymers derived from unsaturated alcohols and amines or from their acyl derivatives or acetals,
   (g) polyurethanes, polyamides, polyureas, polyesters, polycarbonates, polysulfones, polyether-sulfones and polyether-ketones, against the action of light, oxygen and heat, which comprises using for this purpose N-(β-carbonyl- or β-cyanovinyl)-2,2,6,6-tetramethylpiperidine derivatives I as claimed in claims 1–8.

* * * * *

UNITED STATES PATENT AND TRADEMARK OFFICE
CERTIFICATE OF CORRECTION

PATENT NO.  : 5,434,202
DATED       : July 18, 1995
INVENTOR(S) : Alfred KRAUSE, et al.

It is certified that error appears in the above-indentified patent and that said Letters Patent is hereby corrected as shown below:

On the title page, Item [54] and Column 1, Lines 2-4, the title should read:

--N-(BETA-CARBONYL- AND BETA-CYANOVINYL)-2,2,6,6-TETRAMETHYL-PIPERIDINE DERIVATIVES--

Signed and Sealed this

Twelfth Day of September, 1995

Attest:

BRUCE LEHMAN

*Attesting Officer*     *Commissioner of Patents and Trademarks*